United States Patent [19]

Dalglish

[11] Patent Number: 4,690,674
[45] Date of Patent: Sep. 1, 1987

[54] INTRAVENOUS TUBE ASSEMBLY

[76] Inventor: Herbert F. Dalglish, 284 Cherokee Ave., St. Paul, Minn. 55107

[21] Appl. No.: 861,979

[22] Filed: May 12, 1986

[51] Int. Cl.⁴ .......................................... A61M 27/00
[52] U.S. Cl. .............................. 604/93; 128/DIG. 6; 128/DIG. 26; 5/503; 248/51; 248/160
[58] Field of Search .............. 604/174, 326, 181, 322, 604/93; 248/51, 75, 80, 103, 104, 158, 160, 125, 214; 5/503, 508; 128/DIG. 26, DIG. 6

[56] References Cited

U.S. PATENT DOCUMENTS

| 837,642 | 12/1906 | Powell | 5/503 |
|---|---|---|---|
| 1,186,202 | 6/1916 | Jasinski | 5/503 |
| 1,671,085 | 5/1928 | Nuernberg | 248/103 |
| 2,191,782 | 2/1940 | Valane | 5/503 |
| 2,715,002 | 8/1955 | Davis | 248/51 |
| 2,716,531 | 8/1955 | Johnson | 248/51 |
| 3,338,538 | 8/1967 | Roche | 248/75 |
| 3,797,792 | 3/1974 | Huber | 248/125 |
| 4,141,524 | 2/1979 | Corvese, Jr. | 128/DIG. 26 |
| 4,453,933 | 6/1984 | Speaker | 128/DIG. 26 |

FOREIGN PATENT DOCUMENTS

| 3422022 | 12/1985 | Fed. Rep. of Germany | 5/508 |
|---|---|---|---|
| 1046399 | 12/1953 | France | 248/51 |
| 254221 | 4/1948 | Switzerland | 248/51 |
| 205756 | 1/1923 | United Kingdom | 248/51 |
| 1476061 | 6/1977 | United Kingdom | 5/508 |
| 187247 | 11/1966 | U.S.S.R. | 604/181 |

*Primary Examiner*—Stephen C. Pellegrino
*Assistant Examiner*—Ralph A. Lewis
*Attorney, Agent, or Firm*—Burd, Bartz & Gutenkauf

[57] ABSTRACT

An intravenous tube assembly to supply intravenous fluid to a patient includes an intravenous fluid container held by a stand and connected at one end to intravenous fluid tubing, which is connected at the opposite end to a patient. A mast assembly has an elongate resilient mast with a movable tip and a base. The base is fixed to structure proximate the patient. The tip carries a tube holder which releasably holds a segment of the intravenous tube leading to the patient. The mast permits patient movement by deflecting to follow the patient and rebounding upon return of the patient to prevent an excess of residual intravenous tube in the vicinity of the patient.

20 Claims, 7 Drawing Figures

U.S. Patent  Sep. 1, 1987  4,690,674
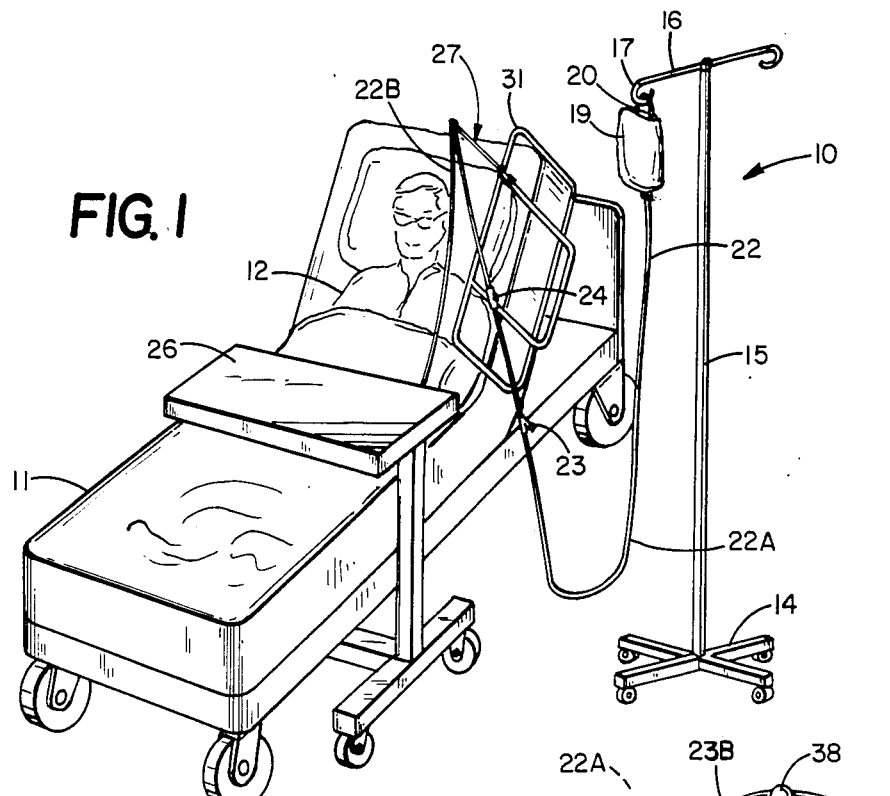
FIG. 1
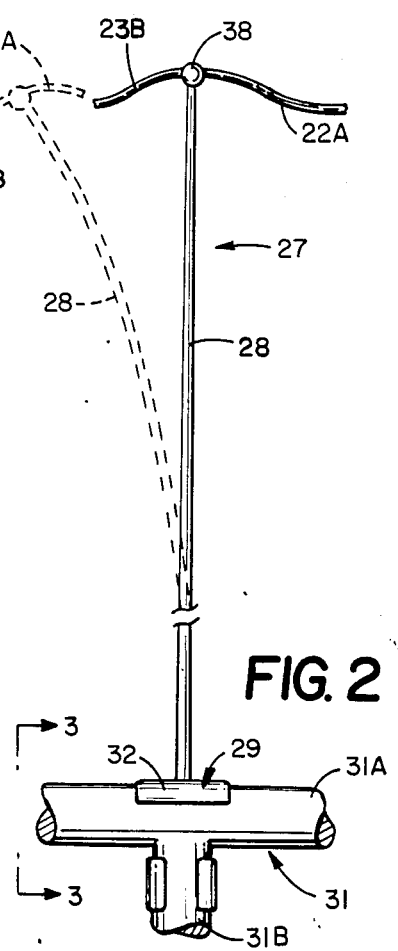
FIG. 2
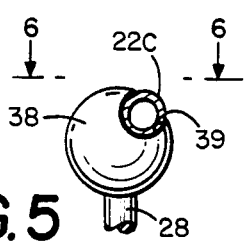
FIG. 5
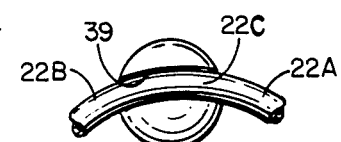
FIG. 6
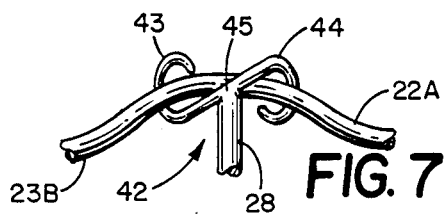
FIG. 7
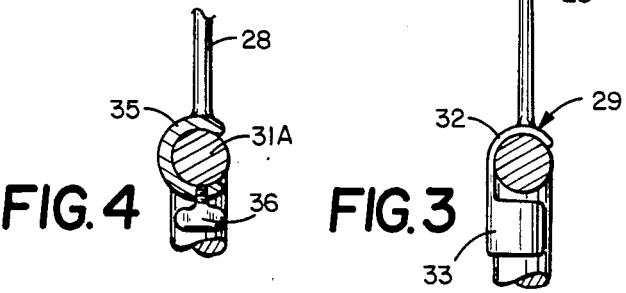
FIG. 4  FIG. 3

INTRAVENOUS TUBE ASSEMBLY

BACKGROUND OF THE INVENTION

Patients in hospitals or otherwise under medical care frequently require a continuous supply of fluid injected directly into the body, the most commonly known procedure being intravenous feeding. A hollow needle secured to the patient, usually at the hand or wrist area, is connected to a tube which carries a nutrient fluid mixture and perhaps other medicinal fluids from a supply container that is usually suspended on a stand, such that fluid flow into the patient is effected under the influence of gravity. The tube is elongate to permit patient movement. Frequently, the tube too readily follows patient movement and becomes entangled, as when the patient rolls over while sleeping or when reaching a distance over the bed. The tube cannot only become entangled causing patient discomfort and distress, but this can also cause the tube to dislodge from the body. Even without such entanglement, the possibility of it is worrisome to the patient.

SUMMARY OF THE INVENTION

The invention pertains to an intravenous tube assembly for delivery of nutrient, medicinal or other fluids to a patient while avoiding an excess of intravenous fluid tubing in the vicinity of the patient. The assembly includes an intravenous fluid container connected to one end of an intravenous fluid tubing. The other end of the tubing is connected to the patient in conventional fashion. An intermediate tubular segment of the tubing is connected to the free or movable tip of an elongate, slender mast that is resiliently deflectable between its ends. The opposite end or base of the mast is secured to fixed structure proximate the patient, such as a bed rail. A first section of tubing extends from the fluid container to the tip of the mast. The second section of the tubing extends from the tip of the mast to the patient. The mast normally stands upright holding the tubing in an out-of-the-way position. The second section of the tubing is a length measured to extend from the tip of the mast in the upright stance to the intended proximity of the patient's hand in a normal relaxed position with some residual length of tubing left over for small normal movements. The mast is readily deflectable. When the patient's hand is moved to a location taking up the residual or slack between the hand and the mast tip, further movement in direction away from the normal upright stance of the mast is permitted by deflection of the mast in direction toward the movement of the hand. Mast deflection occurs under very little tension force from the tubing so as not to disturb the connection of the tubing with the patient. Upon return of the hand to its usual position, the mast rebounds to a normal stance so as not to leave excess residual tubing in the patient vicinity. A tube holder is located at the tip of the mast and frictionally retains a tubular segment. If the pull on the tube holder exceeds a predetermined amount, as when the patient strays too far from the bed, the tubular segment is released by the tube holder before the tube end is pulled from the patient.

IN THE DRAWINGS

FIG. 1 is a perspective view of an intravenous tube assembly of the invention in operative proximity to a hospital bed and a patient located therein;

FIG. 2 is a front elevational view of a portion of the intravenous tube assembly of FIG. 1;

FIG. 3 is an enlarged sectional view of a portion of the intravenous tube assembly shown in FIG. 2 taken along the line 3—3 thereof;

FIG. 4 is a view like that of FIG. 3 showing an alternative clamp assembly for the intravenous tube assembly;

FIG. 5 is an enlarged view of the tip of the mast of the intravenous tube assembly shown in FIG. 2;

FIG. 6 is a top plan view of the tube holder and tip of the mast of FIG. 5 taken along the line 6—6 thereof; and FIG. 7 is a side elevational view of an alternative form of tube holder located at the tip of the mast.

DESCRIPTION OF A PREFERRED EMBODIMENT

Referring to the drawings, there is shown in FIG. 1 an intravenous tubing assembly indicated generally at 10 located proximate a hospital bed 11 and operatively attached to a patient 12 residing in bed 11. Intravenous tubing assembly 10 includes a fluid container support comprised as an upright stand having a four-legged, wheeled pedestal base 14 carrying an elongate upright column 15. A hanger 16 is fixed to the top end of column 15 and has inverted hooks 17 for connection to an intravenous fluid container. An intravenous fluid container or flexible pouch 19 is suspended by a loop 20 from a hook 17 at a location above patient 12 so that fluid can flow by gravity from pouch 19 to the patient 12. Pouch 19 contains a supply of intravenous fluid.

Intravenous fluid tubing extending from pouch 19 to patient 12 includes an elongate continuous intravenous tube 22 that is connected a one end to the lower portion of pouch 19 and at the other end to patient 12 in the vicinity of the hand, wrist or other suitable location by usual and accepted means. Tube 22 has the usual continuous tubular opening to readily transport intravenous fluid. Additional tubes could be provided (not shown), as through a connector 23, in order to introduce other fluids to patient 12 as may be deemed desirable. A closure member 24 can be provided for shutting off flow of intravenous fluid.

Patient 12 is usually confined to bed 11 but normally likes to move around therein without entangling or dislodging intravenous tube 22. This occurs when patient 12 rolls over when sleeping, reads a magazine or newspaper, eats or obtains other objects from table 26, sits on the side of the bed to visit, strolls a short distance from the bed 11 or engages in many like activities.

In order to facilitate such patient activity without entangling or dislodging tube 22, there is provided a tubular support means or mast assembly 27 which releasably holds or retains a segment of tube 22 at a location beneath pouch 19 and at an intermediate location thereon to hold it out of the way and separate it into a first or upstream section 22A connected to pouch 19, and a second or downstream section 22B connected to patient 12. Mast assembly 27 includes an elongate, slender, resilient, deflectable wand or mast 28 connected at the lower end to a base or clamp 29 that is releasably secured to bed rail 31 at a location close to the patient 12. Clamp 29 attaches to the bed rail 31 at a T intersection of an upper cross member 31A and a brace member 31B. Clamp 29 has a curved shoulder 32 (see FIGS. 2 and 3) which extends over the upper portion of the upper rail member 31A. The lower end of the mast 28 is connected to the shoulder 32 at the top portion thereof where it engages the rail 31A. A C-shaped clip 33 is connected to the shoulder 32 and engages the cross member 31B. The C-shaped clip 33 has resilient arms which spread in order to engage and disengage the cross member 31B. The base 29 is readily clipped onto and off of the bed rail 31.

Alternative clamping structure is shown in FIG. 4 wherein there is provided a C-shaped base 35 which surrounds a top bed rail segment 31A. The lower end of mast 28 is connected to the top of the C-shaped base 35 and extends upwardly therefrom. A set screw 36 is threaded into the lower portion of the base 35 diametrically opposite the mast 28 and secures the base in place with respect to the rail segment 31A. The set screw 36 is readily released for removal of the base 35 from the rail segment 31A.

A tube holder 38 is connected to the movable tip of mast 28 and releasably holds a segment 22C of intravenous feeding tube 22 separating it between the upstream and downstream sections 22A, 22B. Tube holder 38 is formed as a sphere having an arcuate groove 39 which has a diameter slightly larger than that of tube 22. A tube segment 22C (see FIGS. 5 and 6) connecting the sections 22A and 22B is located in the groove 39 and frictionally retained therein. The arcuate shape of groove 39 aids in the frictional restraint of the segment 22C. Upon application of a predetermined pull or force, the frictional restraint of the groove 39 is overcome, and the tube 32 is released to slide therein. Downstream section 22B is of a measured length to extend from the tip of mast 28 in undeflected condition to the normal relaxed patient 12 in bed 11 with a residual length left over sufficient to permit some normal patient movement in all directions without deflection of mast 28.

Mast 28 is flexible and resilient, as well as slender, whereby the tip is readily deflected or moved upon application of slight tension force by the downstream tube segment 22B as shown in FIG. 2. The mast 28 readily rebounds to an undeflected, generally upright stance, as shown in FIG. 2 upon release of the pulling force, carrying the tube 22 and tubeholder 38 with it. Mast 28 is preferably about thirty inches (76 cm) long and can be formed of metal, glass fiber or other resilient material.

FIG. 7 shows an alternative form of tube holder 42 at the upper tip of mast 28. The tube holder 42 is generally in the form of an inclined FIG. 8 with open loops, having a first loop 43 and a second loop 44 connected by a stem 45, which also connects to the top of mast 28. The intravenous tube 22 is trained through the first and second loops 43, 44 with an intermediate section frictionally retained therein. The loops 43, 44 are open at ends opposite the stem 45 for insertion and removal of the intermediate tube segment 22. A tension force on the tube 22 will pull the tube holder 42 causing deflection of the mast 28 to a predetermined limit. Upon further exertion of force, the frictional restraint imposed by the tube holder 42 is overcome so that the tube 22 is movable therein to follow the patient before endangering the tubular connection to the patient.

In use, mast assembly 27 is fixed to the hospital bed 11 proximate the patient 12. The bed can be in an inclined position, as shown in FIG. 1, or in a normal reclined position. The mast assembly could also be fixed proximate a patient's chair or such other location convenient to the patient. The downstream tubular segment 22B is measured to be of a sufficient length to connect to the patient 12 at the usual intended location and fashion, and have a residual length left over for normal hand and wrist motion in the vicinity of the bed. Movement beyond a normal slight movement takes up the residual length of tube 22B and is followed by a deflection of the mast 28. Upon deflection of the mast 28, the patient can sit on the side of the bed or even stand, move about a limited amount enabling the patient to read, eat, switch a light on and off or the like. When the patient returns to the normal position in the bed, the mast 28 rebounds to a generally upward stance leaving only the normal residual length of the downstream section 22B, whereby the tube does not become entangled with the patient or other surrounding items. Should the patient wander too far while the mast 28 is deflected, the force holding the tube by the tube holder is overcome such that the tube slides or is released with respect to the tube holder before the tube is pulled away from the patient. At any time, the intravenous tube is readily inserted or detached from the tube holder as the need may be as when the patient will travel up and down a hallway taking the stand 11 along.

While there have been shown certain embodiments of the invention, it will be apparent that deviations can be had therefrom without departing from the scope and the spirit of the invention.

The embodiments of the invention in which an exclusive property or privilege is claimed are defined as follows:

1. An intravenous tube assembly for providing fluid intravenously to a patient, comprising:
   a stand having an elongate vertical column supported on a pedestal base at a lower end thereof and having a hanger member at the upper end thereof;
   an intravenous fluid container comprised as a flexible pouch suspended from the hanger member of the stand for containing a supply of intravenous fluid;
   intravenous fluid tubing, having a first end operatively connected to the fluid container, and a second end connectable to a patient for intravenous receipt of fluid by the patient;
   a mast assembly having an elongate, resiliently deflectable mast, a base, said mast having a fixed end secured to the base and a movable tip deflectable with respect to the base, and a tube holder located on the movable tip of the mast, said tube holder having means releasably retaining an intermediate tubular segment of the fluid tubing between the first and second ends;
   said base of the mast assembly having means for securing the mast assembly on a structure proximate the patient with the mast holding the intermediate tube segment out of the way of the patient and positioned for deflection toward the patient upon movement by the patient away from the mast beyond a predetermined distance;
   said tubing section between the tube holder on the mast and the second end being a measured length to extend from the top of the undeflected mast to the normal relaxed position of the patient with some residual tubing to accommodate limited normal patient movement before deflection of the mast upon additional movement in a direction away from the mast.

2. The intravenous tube assembly of claim 1 wherein: said base includes a releasable clamp for releasably securing the mast assembly on structure proximate the patient.

3. The intravenous tube assembly of claim 2 wherein: said clamp is C-shaped for installation on a rail-type member and includes a set screw for fixing the position of the clamp.

4. The intravenous tube assembly of claim 2 wherein: said clamp has a shoulder extendible over a first rail member, and a resilient C-shaped clip for engagement of a second rail member intersecting the first rail member, said mast being fixed to the shoulder.

5. The intravenous tube assembly of claim 1 wherein: said tube holder includes a member having an arcuate groove with a diameter slightly larger than the diameter of the tubular segment, said tubular segment being frictionally retained in said arcuate groove.

6. The intravenous tube assembly of claim 5 wherein: said tube holder member is spherical in shape.

7. The intravenous tube assembly of claim 1 wherein: said tube holder is formed as a member having first and second loops, said tubular segment being trained through the first and second loops and frictionally retained therein.

8. The intravenous tube assembly of claim 7 wherein: said loops have open portions for insertion and removal of the tubular segment.

9. The intravenous tube assembly of claim 1 wherein: said mast is approximately 30 inches in length.

10. An intravenous tube assembly to provide fluid intravenously to a patient, comprising:
fluid container means comprised as a flexible pouch;
container support means including an elongate vertical column supported on a pedestal base at a lower end thereof and having a hangar member at the upper end thereof, said fluid pouch suspended from the hanger member;
intravenous fluid tubing having a first end operatively connected to the flexible pouch and a second end connectable to a patient;
tubular support means for retaining an intermediate segment of the tubing between the first end and the second end and holding it out of the way of the patient and permitting limited normal patient movement, said support means including an elongate, slender mast resiliently deflectable between first and second mast ends;
means on the second end of the mast retaining said intermediate segment of tubing;
means on the first end of the mast for securing it to fixed structure permitting deflection of the second end and positioning the second end of the tubing proximate the patient while holding the intermediate tube segment out of the way of the patient and deflectable toward the patient upon movement by the patient away from the second end of the mast beyond a predetermined distance.

11. The intravenous tube assembly of claim 10 wherein: said tubing section between the means on the second end mast and the second end is a measured length to extend from the tip of the undeflected mast to the normal relaxed position of the patient with some residual tubing to accommodate limited normal patient movement before deflection of the mast upon additional movement in a direction away fom the mast.

12. The intravenous tube assembly of claim 11 wherein: said means on the first end of the mast includes a releasable clamp for releasably securing the mast assembly on structure proximate the patient.

13. The intravenous tube assembly of claim 12 wherein: said mast is approximately 30 inches long.

14. The intravenous tube assembly of claim 11 wherein: the means on the second end of the mast includes a spherical member having an arcuate groove with a diameter slightly larger than the diameter of the tubular segment, said tubular segment being frictionally retained in said arcuate groove.

15. The intravenous tube assembly of claim 11 wherein: said means on the second end of the mast is formed as a member having first and second loops, said tubular segment being trained through the first and second loops and frictionally retained therein.

16. The intravenous tube assembly of claim 15 wherein: said loops have open portions for insertion and removal of the tubular segment.

17. The intravenous tube assembly of claim 10 wherein: said mast is approximately 30 inches long.

18. An intravenous tube assembly for providing fluid intravenously to a patient, comprising:
stand means;
an intravenous fluid container connected to the stand means for containing a supply of intravenous fluid;
intravenous fluid tubing, having a first end operatively connected to the fluid container, and a second end connectable to a patient for intravenous receipt of fluid by the patient;
a mast assembly having an elongate, resiliently deflectable mast, a base, said mast having a fixed end secured to the base and a movable tip deflectable with respect to the base, and a tube holder located on the movable tip of the mast, said tube holder having means releasable retaining an intermediate tubular segment of the fluid tubing between the first and second ends;
said base of the mast assembly having a releasable clamp for releasably securing the mast assembly on structure proximate the patient with the mast holding the intermediate tube segment out of the way of the patient and positioned for deflection toward the patient upon movement by the patient away from the mast beyond a predetermined distance, said clamp having a shoulder extendible over a first rail member, and a resilient C-shaped clip for engagement of a second rail member intersecting the first rail member, said mast being fixed to the shoulder;
said tubing section between the tube holder on the mast and the second end being a measured length to extend from the tip of the undeflected mast to the normal relaxed position of the patient with some residual tubing to accommodate limited normal patient movement before deflection of the mast upon additional movement in a direction away from the mast.

19. An intravenous tube assembly for providing fluid intravenously to a patient, comprising:
stand means;
an intravenous fluid container connected to the stand means for containing a supply of intravenous fluid;
intravenous fluid tubing, having a first end operatively connected to the fluid container, and a second end connectable to a patient for intravenous receipt of fluid by the patient;
a mast assembly having an elongate, resiliently deflectable mast, a base, said mast having a fixed end secured to the base and a movable tip deflectable with respect to the base, and a tube holder located on the movable tip of the mast, said tube holder having means releasably retaining an intermediate tubular segment of the fluid tubing between the first and second ends;

said tube holder including a spherical member having an arcuate groove with a diameter slightly larger than the diameter of the tubular segment, said tubular segment being frictionally retained in said arcuate groove;

said base of the mast assembly having means for securing the mast assembly on structure proximate the patient with the mast holding the intermediate tube segment out of the way of the patient and positioned for deflection toward the patient upon movement by the patient away from the mast beyond a predetermined distance;

said tubing section between the tube holder on the mast and the second end being a measured length to extend from the tip of the undeflected mast to the normal relaxed position of the patient with some residual tubing to accommodate limited normal patient movement before deflection of the mast upon additional mvoement in a direction away from the mast.

20. An intravenous tube assembly to provide fluid intravenously to a patient, comprising:

fluid container means;

container support means releasably supporting the fluid container means;

intravenous fluid tubing having a first end operatively connected to the container means and a second end connectable to a patient;

tubular support means for retaining an intermediate segment of the tubing between the first end and the second end and holding it out of the way of the patient and permitting limited normal patient movement, said support means including an elongate, slender mast resiliently deflectable between first and second mast ends;

means on the second end of the mast retaining said intermediate segment of tubing, said means including a spherical member having an arcuate groove with a diameter slightly larger than the diameter of the tubular segment, said tubular segment being frictionally retained in said arcuate groove;

means on the first end of the mast for securing it to fixed structure permitting deflection of the second end and positioning the second end of the tubing proximate the patient while holding the intermediate tube segment out of the way of the patient and deflectable toward the patient upon movement by the patient away from the second end of the mast beyond a predetermined distance;

said tubing section between the means on the second mast end and the second tubing end being a measured length to extend from the second end of the undeflected mast to the normal relaxed position of the patient with some residual tubing to accommodate limited normal patient movement deflection of the mast upon additional movement in a direction away from the mast.

* * * * *